(12) United States Patent
Phelan

(10) Patent No.: US 9,719,934 B2
(45) Date of Patent: Aug. 1, 2017

(54) READING OF ASSAYS

(71) Applicant: ALERE SWITZERLAND GMBH, Zug (CH)

(72) Inventor: Andrew Peter Phelan, Cranfield (GB)

(73) Assignee: ALERE SWITZERLAND GMBH, Zug (CH)

( * ) Notice: Subject to any disclaimer, the term of this patent is extended or adjusted under 35 U.S.C. 154(b) by 228 days.

(21) Appl. No.: 14/354,474

(22) PCT Filed: Oct. 2, 2012

(86) PCT No.: PCT/GB2012/052430
§ 371 (c)(1),
(2) Date: Apr. 25, 2014

(87) PCT Pub. No.: WO2013/061026
PCT Pub. Date: May 2, 2013

(65) Prior Publication Data
US 2014/0301898 A1 Oct. 9, 2014

(30) Foreign Application Priority Data
Oct. 25, 2011 (GB) .................................. 1118405.8

(51) Int. Cl.
*G01N 21/27* (2006.01)
*G01N 21/75* (2006.01)
(Continued)

(52) U.S. Cl.
CPC ........... *G01N 21/75* (2013.01); *G01N 21/274* (2013.01); *G01N 21/8483* (2013.01);
(Continued)

(58) Field of Classification Search
None
See application file for complete search history.

(56) References Cited

U.S. PATENT DOCUMENTS

| | | | |
|---|---|---|---|
| 6,055,060 A | 4/2000 | Balduan et al. | |
| 6,707,554 B1 | 3/2004 | Miltner et al. | |

(Continued)

FOREIGN PATENT DOCUMENTS

| | | |
|---|---|---|
| EP | 1484601 A2 | 12/2004 |
| EP | 2031376 A2 | 3/2009 |
| WO | 2011048381 A1 | 4/2011 |

OTHER PUBLICATIONS

International Search Report of PCT/GB2012/052430, mailed Jan. 28, 2013, the whole document.

*Primary Examiner* — Neil N Turk
(74) *Attorney, Agent, or Firm* — Steptoe & Johnson LLP

(57) ABSTRACT

Disclosed is an assay result reading apparatus for use with an assay in which a detectable substance tends to accumulate within a detection zone of the assay, the reading apparatus comprising: a housing or baffle, having a window therein; a light source which emits light through the window so as to illuminate the detection zone of the assay; and a light detector to detect the amount of light reflected and/or transmitted by the detection zone, which amount is at least partly dependent on the amount of detectable substance accumulated in the detection zone; wherein the shape of the window is adapted to render the reading apparatus less sensitive, preferably insensitive, to minor mis-positioning of the detection zone relative to one or more of the window, the light source and the light detector.

7 Claims, 5 Drawing Sheets

(51) Int. Cl.
  *G01N 21/84*    (2006.01)
  *B01L 3/00*     (2006.01)
  *G01N 21/78*    (2006.01)

(52) U.S. Cl.
  CPC ............ *B01L 3/5023* (2013.01); *G01N 21/78* (2013.01); *Y10T 29/49826* (2015.01)

(56) References Cited

U.S. PATENT DOCUMENTS

| | | |
|---|---|---|
| 2003/0119202 A1 | 6/2003 | Kaylor et al. |
| 2005/0036148 A1* | 2/2005 | Phelan ............... G01N 21/8483 356/446 |
| 2007/0013910 A1* | 1/2007 | Jiang ................. G01N 15/0205 356/336 |
| 2010/0007879 A1* | 1/2010 | Mavliev ............. G01N 15/1459 356/336 |

* cited by examiner

READING OF ASSAYS

CLAIM FOR PRIORITY

This application claims priority under 35 USC 371 to International Application No. PCT/GB2012/052430, filed on Oct. 2, 2012, which claims priority to British Patent Application No. 1118405.8, filed on Oct. 25, 2011, each of which is hereby incorporated by reference in its entirety.

FIELD OF THE INVENTION

The present invention relates to a reader for an assay, more especially a reader for an assay in which a detectable substance tends to accumulate in a detection zone of the assay. The invention also relates to a method of making an assay reader, and to a method of reading an assay.

BACKGROUND TO THE INVENTION

It is well known to use cheap, disposable assay devices to detect the presence and/or amount of an analyte in a sample and these assay devices in particular lend themselves for use in the home and/or at point-of-care. Such devices tend to be either lateral flow assay devices or microfluidics assay devices.

Typically, lateral flow assay devices, such as those disclosed in EP291194, are of the type in which a liquid sample is applied, directly or (more usually) indirectly, to a porous matrix, such as a nitrocellulose or paper filter. The liquid sample migrates along the porous matrix, generally mobilising a dried assay reagent or component (typically a labelled antibody such as a particulate labelled antibody) releasably immobilised on the porous matrix. Typically the labelled antibody forms a complex with the analyte of interest in the sample, which labelled complex is usually then captured in a detection region of the porous matrix, by a second antibody for the analyte of interest. Accumulation of the labelled binding reagent in the detection region or zone is therefore indicative of the presence, or extent of analyte in a liquid sample. It will be appreciated that other variants of lateral flow assays exist, in particular competition format assays in which a labelled reagent tends to be captured in the detection zone if the analyte is absent from the sample.

Detection of labelled reagent at the detection zone may be carried out visually or by means of a photodetector. Visual read, non-electronic, assay devices have the advantage of being low cost, however a problem associated with such assay devices, especially pregnancy-testing devices and/or home-use assay devices, is that they provide an assay result as a signal of variable strength, which can require a degree of interpretation. This leaves the assay result open to misinterpretation, especially where the user or reader of the assay device has a preferred assay result in mind, especially in the case of a pregnancy test, where the user may have little or no experience of using such an assay device and may be in a heightened emotional state.

As a consequence, electronic digital devices have been developed wherein the presence or amount of the labelled reagent is determined by means of a photodetector and the result of the assay displayed on e.g. an LCD display. Such digital devices have the advantage in that they provide an unambiguous result such as "YES" or "NO", or a numerical range or value, which does not require interpretation. Such devices may be single use and therefore disposable. The assay reader reads the assay by measuring the amount of detectable substance accumulated in the detection zone, typically, but not necessarily, by measuring the reflectance from, or transmission of light through, the detection zone. The lateral flow assay test strip may be inserted into the reader before or after application of the sample, or the test strip may be an integral part of the reader.

In a microfluidics assay device, many of the same principles as used in a lateral flow assay may be employed. However, instead of the liquid sample being applied to a porous matrix, the sample is applied or fed into a conduit or channel, along which the liquid advances, usually by means of capillary action. A detection zone may be provided on an inner surface of the channel on which, for example, an immobilised binding reagent is provided. Again, the result of the assay may be determined non-electronically, by visual inspection, or by an electronic assay result reader.

SUMMARY OF THE INVENTION

Typically, electronic assay reading devices currently available utilise a rectangular window which frames the detection zone being read and prevents light reaching and/or being reflected from irrelevant or inappropriate portions of the test strip or microfluidics assay device. The window used is wider than the detection zone, so as to allow for some mechanical assembly tolerances which are present in the manufacturing processes of the test strip, or the microfluidics assay device, and the assay reader. This ensures that the detection zone of the assay will always fall within the window.

The present inventor has discovered a problem with this approach, which problem does not appear previously to have been appreciated.

Specifically, it is found that the sensitivity of the measurement depends to some degree upon the position of the detection zone within the window due to the configuration of the light source used to illuminate the detection zone and the light detector used to detect light reflected by and/or transmitted through the detection zone.

In effect, different loci within the window have different sensitivities. That is, a constant density of label or the like within the window does not generate a constant level of signal, because the illumination of (e.g. the test strip within) the window may not be entirely uniform and/or the amount of light reflected or transmitted from the different loci, within the window, and detected by the light detector, is not constant. The amount of light falling on any particular area of the window will depend on the geometrical arrangement of the light source and detector relative to the window.

The detection zone can be relatively displaced from its intended position as a result of any one or more of a variety of errors. For example, especially in a lateral flow assay, the detection zone typically comprises a thin line or other deposit of an immobilized 'capture' antibody, and which binds a labelled complex. The capture antibody may be deposited slightly out of position. Alternatively, the assay device used to perform the assay may be inaccurately positioned when engaged with the assay result reader, either during manufacture (e.g. if the consumer is supplied with apparatus in which the assay device forms an integral part of the assay result reader) or during use (e.g. if the consumer is supplied with a separate test dipstick or lateral flow assay strip, which must be inserted into the assay result reading device in order for the assay result to be read). As an illustrative example, in some embodiments of the prior art, as the detection zone is displaced from the centre of the window (in either direction), away from its intended location, effective discrimination of the zone falls off and the signal will be read as having a weaker intensity than if it had been placed at the centre of the window. This is illustrated schematically in FIGS. 1 & 2. The present invention aims to overcome or reduce problems of this type.

In a first aspect the invention provides an assay result reading apparatus for use with an assay in which a detectable substance tends to accumulate within a detection zone of the assay, the reading apparatus comprising: a housing or baffle, having a window therein; a light source which emits light through the window so as to illuminate the detection zone of the assay; and a light detector to detect the amount of light reflected and/or transmitted by the detection zone, which amount is at least partly dependent on the amount of detectable substance accumulated in the detection zone; wherein the shape of the window is adapted to render the reading apparatus less sensitive, preferably insensitive, to minor mis-positioning of the detection zone relative to one or more of the window, the light source and the light detector.

In particular embodiments, the reading apparatus is less sensitive, preferably insensitive, to minor mis-positioning of the detection zone relative to the window. However, the window, light source and light detector will normally be in a fixed position relative to one another, such that movement of the detection zone, relative to (e.g.) the window, will normally also inevitably constitute movement of the detection zone relative to the light source and the detector.

The term "light" in the present specification is intended to refer to any part of the electromagnetic spectrum which might usefully be employed in detecting a signal in a detection zone (including e.g. ultra-violet, infra-red or even radio waves), and the terms "light source" and "light detector" are to be construed accordingly. In preferred embodiments the light source will emit light in that part of the electromagnetic spectrum which is visible to a normal human observer, and the detection zone will preferably reflect and/or transmit detectable amounts of light in the visible spectrum, with the light detector similarly detecting light in the visible part of the spectrum. However, it is at least conceivable that other parts of the electromagnetic spectrum could be used. Thus, for example, if the detectable substance is one which is detectable using infra-red or ultra-violet radiation, then the "light" detector should be sensitive to a corresponding region of the electromagnetic spectrum.

For present purposes, the reader is "insensitive" to minor mis-positioning if for a fixed intensity of light energy output from the light source, and for a fixed amount of detectable substance in the detection zone, the amount of light detected by the light detector varies by less than 10%, less than 9%, less than 8%, preferably less than 7%, 6%, 5%, 4%, 3%, 2% or even less than 1%, for displacements of the detection zone, relative to the window, of +/−0.1 mm, 0.2 mm, 0.3 mm, 0.4 mm or even up to +/−0.5 mm. "Minor mis-positioning" of the detection zone relative to the window will be understood to refer to displacement of +/−0.1 mm of the detection zone from its intended position (which will usually be on, or along, a central axis of the window), or even a displacement of up to +/−0.2 mm, 0.3 mm, 0.4 mm or even +/−0.5 mm. Displacements greater than +/−0.5 mm are relatively large and generally unlikely to occur or, if they do occur, will be apparent in quality control checks and so are unlikely to be present in a device reaching a consumer.

The displacement of the detection zone for which compensation can be made, by adjusting the window shape in accordance with the invention, will normally be in a substantially or essentially horizontal plane, (i.e. be largely a "side-to-side" displacement) but may also comprise an up/down displacement.

The shape of the window necessary to achieve the desired reduced sensitivity to minor mis-positioning will vary according to the relative positioning of the light source, the detector and the window. Accordingly it is not possible to define the desired shape of the window in general structural terms, and the aforementioned functional definition must suffice. It will, however, be apparent to the person skilled in the art how to perform the invention and obtain the benefit thereof from the disclosure of the present specification and with recourse to the common general knowledge of the person skilled in the relevant art. In many embodiments, the window framing the detection zone will not be rectangular, in contrast to the window shape most usually present in conventional devices. Further guidance is given in Example 4.

The assay may be a microfluidics assay or may be a lateral flow assay. The assay may be a separate device which is introduced into the assay reader in order for the assay result to be read, such as a lateral flow test strip or a dipstick test strip. In such embodiments, the assay result reading apparatus may be formed with a slot or other opening to accommodate insertion of the separate assay device into the result reading apparatus. Conveniently the slot or opening will be so shaped and dimensioned as to permit an assay device to be successfully inserted only in the appropriate orientation. Alternatively, the assay may be an integral part of the reader. If forming an integral part of the reader, the assay may again comprise a microfluidics assay or a lateral flow assay.

The sample applied to the assay device will typically be a liquid sample, and may comprise a sample of food or drink, an environmental sample (e.g. a swab of a surface, a water sample) or may comprise a body fluid, such as saliva, urine, whole blood, plasma, sweat, or a mucosal secretion.

In one embodiment, the detectable substance is an optically detectable substance. In one embodiment, the detectable substance comprises a labelled reagent, such as a binding partner labelled with a label. The binding partner may exhibit a binding affinity for an analyte of interest or for an analogue of an analyte of interest.

In one embodiment the detectable substance comprises a direct label, such as a dye or a gold particle. Accumulation of a substance labelled in this way will have a detectable impact on the amount of light reflected or transmitted by the detection zone.

Depending on the format of the assay, the detectable substance may tend to accumulate in the detection zone in the presence, or in the absence, of an analyte of interest in a sample tested by the assay.

For example, in a "sandwich assay" format, the accumulation of a labelled substance in the detection zone indicates the presence of the analyte of interest in the sample. Conversely, in a "competition assay" format, the accumulation of a labelled substance in the detection zone is usually indicative of the relative absence of the analyte of interest in the sample. The present invention is suitable for both sandwich and competition assay formats, and indeed any other assay format which involves the accumulation of a detectable substance in a detection zone as an indicator of the presence, absence or amount of an analyte of interest in the sample.

The light source, in one embodiment, comprises or consists of a light emitting diode (LED). In the same or another embodiment the detector comprises a photodetector, such as a photodiode. In some embodiments the detector will detect light reflected from the detection zone. In other embodiments the detector will detect light transmitted by the detection zone. The assay result reading apparatus may comprise a plurality of light sources, such as LEDs, and/or may comprise a plurality of photodetectors. More specifically, the reading apparatus may comprise a plurality of LEDs which illuminate the detection zone or the detection zone may be illuminated by a single LED. Other light sources or LEDs may illuminate other parts of the assay device. Light reflected or transmitted by the detection zone may be measured by a single photodetector or by a plurality thereof.

Reflected light and/or transmitted light may be measured by the photodetector. For the present purposes, reflected light is taken to mean that light from the light source is reflected from the detection zone onto the detector. In this situation, the detector is typically provided on the same side of the assay as the light source (e.g. light source and detector both above the assay, or both below the assay). Transmitted light refers to light that passes through the detection zone and typically the detector is provided on the opposite side of the detection zone to the light source (e.g. light source below the assay and detector above the assay, or vice versa). For the purposes of a reflectance measurement, the detection zone may optionally be provided with a backing such as a white reflective MYLAR® plastic layer. Thus light from the light source will fall upon the detection zone, some will be reflected from its surface and some may penetrate into the detection zone and be reflected at any depth up to and including the depth at which the reflective layer is provided. Thus, a reflectance type of measurement may actually involve transmission of light through at least some of the thickness of the detection zone.

In preferred embodiments, the assay reading device will comprise a baffle which is opaque to the wavelength of electromagnetic radiation produced by the light source and/or detected by the light detector. Conveniently, the light detector is sensitive to light in the visible part of the electromagnetic spectrum, and the baffle is an optical baffle (i.e. is opaque and does not transmit light in the visible part of the spectrum). Suitable materials for such an optical baffle include dense black or dark-coloured synthetic plastics resins, such as PPO ("poly phenylene oxide", strictly poly phenylene ether). The baffle desirably defines the reading window of the assay result reading device. It may also perform additional functions, such as shielding adjacent channels from each other, holding the test strip in place, and maintaining the correct distance between the test strip and the light source and/or light detector.

In preferred embodiments the assay reading device may comprise a housing. It is conceivable that, in some embodiments of the invention, the housing, rather than a baffle, defines the reading window. It is generally preferred however that the window is defined by a baffle, and that the assay result reader further includes a housing. The function of the housing, in preferred embodiments, is to hold the components of the reader together, and/or to protect them against the external environment (and, especially to exclude ambient light from the interior of the reader). Like the baffle, the housing may advantageously be formed from a synthetic plastics resin. The housing may desirably be formed from a carbon-loaded plastic such as polystyrene or ABS (Acrylonitrile butadiene styrene).

Typically, both the baffle and the housing are formed by injection moulding.

As explained elsewhere, the shape of the window necessary to achieve the desired insensitivity to relative mispositioning of the detection zone, can be determined with the benefit of the present disclosure. Routine experimentation can be performed, if necessary, to assist in this regard. For example, a fixed level of illumination can be applied to an assay detection zone (the detection zone comprising a fixed amount of a detectable substance), and the detection zone placed at different known positions relative to the window, and the relative signal intensity recorded by the detector measured. This can be used to generate a "map" of relative signal intensity for different relative displacements of the detection zone from the central axis of the window. The shape of the window can then be adjusted to provide an inverse effect, thus counter-acting the effect of the displacement, such that if a displacement in a particular direction tends e.g. to reduce the measured signal intensity, the area of the window can be made larger in that dimension by a corresponding amount.

The window may be shaped to compensate for relative displacement of the detection zone along the major, long ("x") axis of the assay result reading device, or to compensate for relative displacement of the detection zone along the minor, short ("y") axis of the reading device, the x and y axes typically being at right angles to each other. In one embodiment the window may be shaped so as to compensate for relative displacement of the detection zone along both the x and y axes.

Typically the x and y axes are in a substantially or essentially horizontal plane.

The assay result reading apparatus may additionally comprise a further window, which frames a further zone of the assay, which zone may be for example a reference zone or a control zone, in which zones a detectable substance may tend to accumulate when the assay is performed. For example, it is conventional to provide an assay device with a detectable control reagent, which should accumulate in a control zone when the assay is correctly performed, substantially irrespective of the presence or absence of the analyte of interest in the sample. The sensitivity of the reading apparatus for a control or reference zone signal is of far less importance but it may nevertheless be advantageous to utilise the features of the invention to render a control or reference signal reading insensitive to minor mispositioning of the control or reference zone relative to the respective control or reference window.

In a second aspect the invention provides a method of making an assay result reading apparatus, the method comprising the steps of assembling at least one light source and at least one light detector, together with a housing or optical baffle, the housing or optical baffle defining a window through which an assay detection zone is illuminated by the light source, wherein the shape of the window is adapted to render the reading apparatus less sensitive to minor mispositioning of the detection zone relative to the window.

Typically performance of the method of the second aspect of the invention provides an assay result reading apparatus in accordance with the first aspect of the invention as herein defined above.

It is intended and should be appreciated that embodiments may be variously combined or separated without departing from the invention, unless the context dictates otherwise. For the avoidance of doubt, it is expressly stated that features of the invention disclosed herein in relation to one embodiment of the invention may be combined with any one or more other features of the invention disclosed in relation to other embodiments of the invention, unless the context dictates otherwise.

The invention will now be further described by way of illustrative examples and with reference to the accompanying drawings, in which:

EXAMPLES

Example 1

Prior Art

Figure 1:
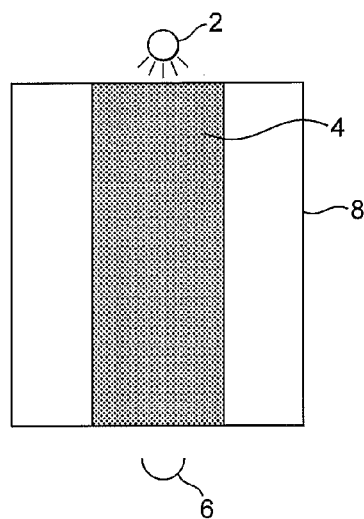
FIG. 1 is a schematic representation, in plan view, of part of a prior art assay result reading apparatus, indicating the configuration of light source, detector, window and detection zone.
Figure 2:
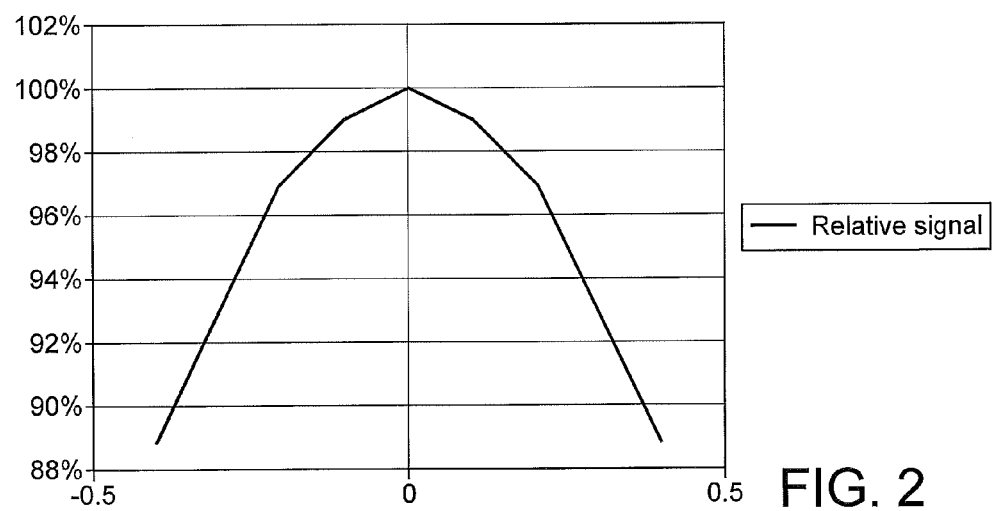
FIG. 2 is a typical graph of relative signal intensity (%) against horizontal displacement (in mm) of an assay device detection zone from its intended position in a prior art reader device configuration of the sort shown in FIG. 1.

The sensitivity of an assay result reading apparatus depends on the relative position of the detection zone within the window. For example, as in FIG. 1, which depicts the situation in which a light source (2), window (8), and an optical detector (6) are all substantially co-axial in plan view, displacement of the detection zone (4) off-centre to the left or to the right, will tend to result in a reduction in the amount of light which follows a path from the light source, to the detection zone, and thence to the optical detector. This leads to an apparent reduction in signal intensity detected by the optical detector, the magnitude of the reduction in intensity being proportional to the relative displacement of the detection zone, yielding results of the sort illustrated in FIG. 2. FIG. 2 is a graph of hypothetical results showing relative signal intensity (%) against displacement (in mm) of a 1 mm detection zone to the left or to the right of the axis of a 2 mm wide window.

This "roll-off" in signal leads to variability in the determined result of the assay and applies both to the situation where one reading apparatus is used to read multiple assays, or where each of a plurality of result readers reads a single assay device.

Example 2

This example is in accordance with the invention and relates to a window shape for an assay result reading apparatus which aims to avoid or reduce the problem of signal roll-off associated with prior art devices as explained in the preceding example.

Figure 3:
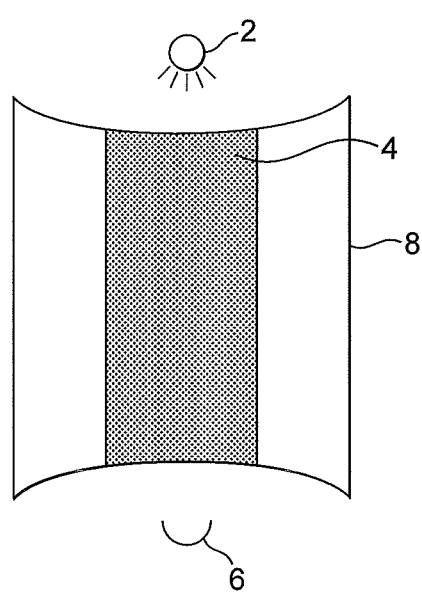
FIG. 3 is a schematic representation, in plan view, of part of one embodiment of assay result reading apparatus in accordance with the present invention, having the configuration of light source, detector and detection zone shown in FIG. 1, but with a window shaped so as to reduce the sensitivity of the reading apparatus to minor mis-positioning of the assay device detection zone relative to the window.

For the embodiment in which the light source (2) and the detector (6) lie on the intended central vertical axis of the detection zone (4), the signal roll-off is substantially symmetrical, whether the detection zone is displaced to the left or the right. Accordingly, an appropriately shaped window to counteract the signal roll-off will also be substantially symmetrical about its central vertical axis, as illustrated in plan view in FIG. 3. Referring to FIG. 3, it can be seen that the window (8) has parallel left and right sides, and concave top and bottom edges, such that the window is shortest in a central region, and increases in length in a symmetrical manner towards the left and right sides. The amount of curvature of the top and bottom edges can be increased or decreased, as desired, to exactly offset the signal roll-off that would otherwise occur as the detection zone (4) is displaced to the left or right of its intended position.

The solution provided by the present invention is technically very simple and requires no additional components and can therefore readily be implemented.

Figure 4:
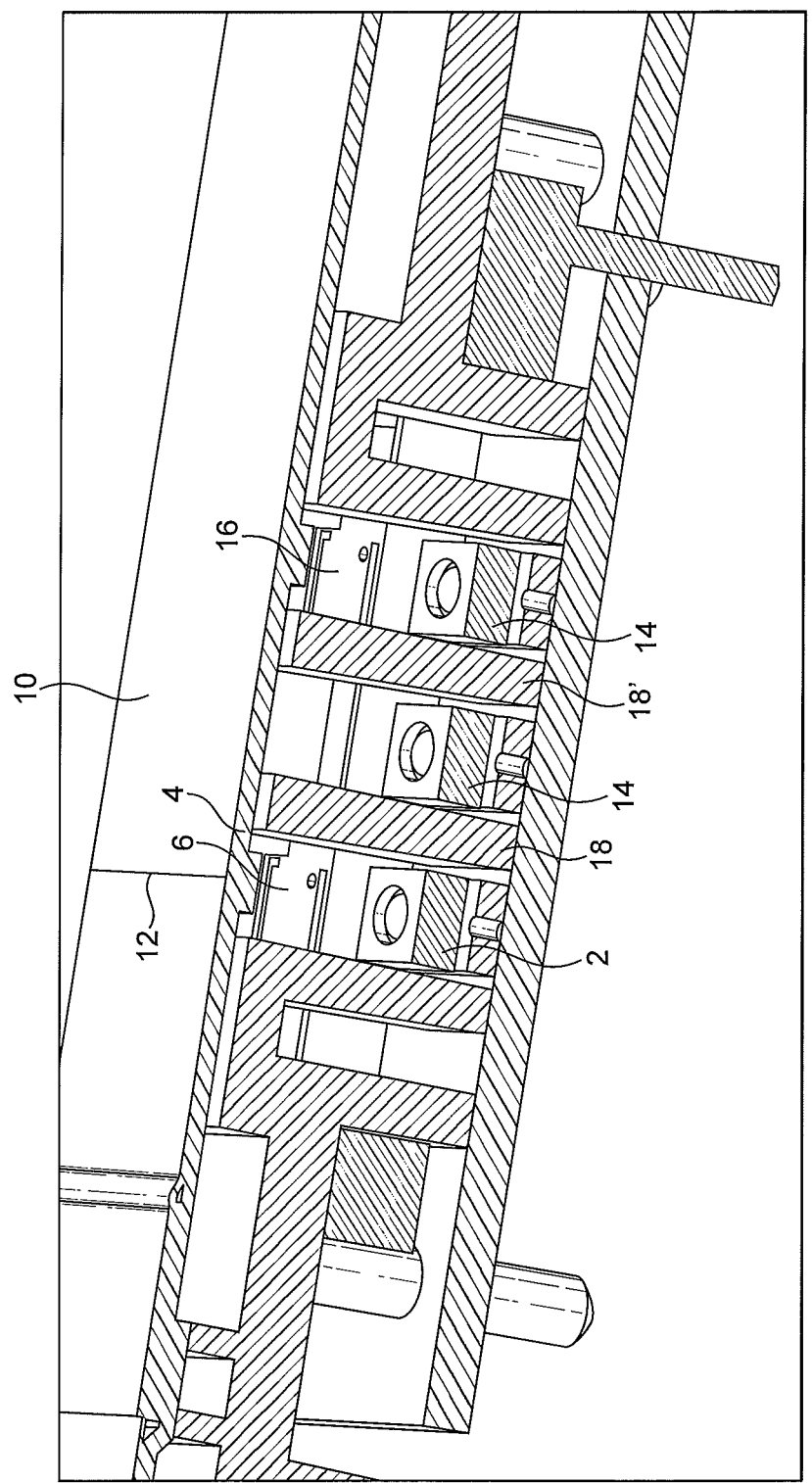
FIG. 4 is a perspective view, partially cut away, of part of a prior art assay result reading apparatus, having the configuration illustrated schematically in FIG. 1.
Figure 5:
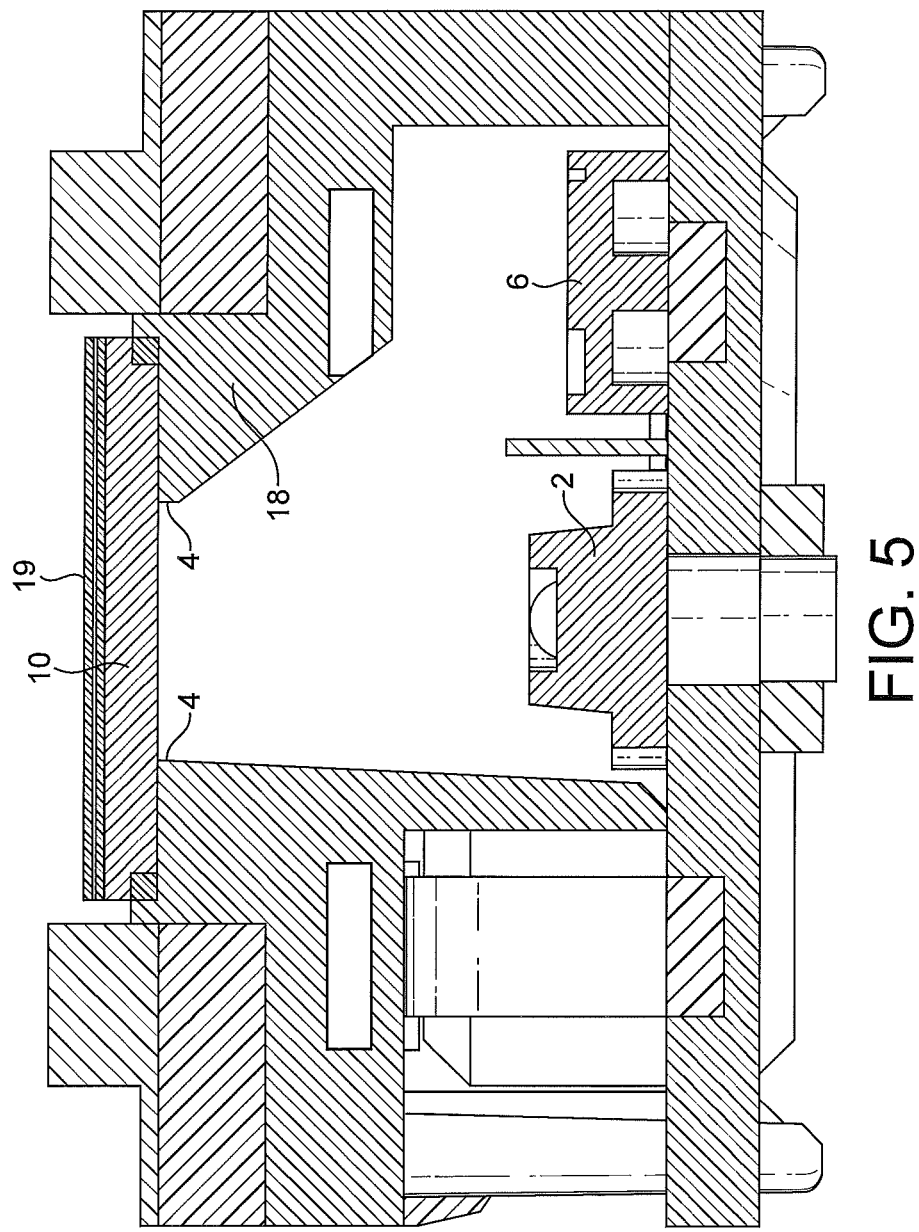
FIG. 5 is an end view, in section, of part of the prior art assay result reading apparatus illustrated in FIG. 4.

FIGS. 4 and 5 are partly sectional illustrations of part of an assay result reading apparatus having the configuration of light source (LED 2), detector (photodiode 6) and detection zone (4). Thus, FIG. 4 is a perspective view showing the arrangement of the light source (LED 2) and detector (photodiode 6), which are both aligned with, and below, the intended central axis (12) of the detection zone on lateral flow test strip (10), which is located within the reading device. The reading device also comprises further LEDs (14) and a further photodiode (16), which are used to interrogate a control/reference zone (not shown) on the test strip (10). The optical baffle (18) defines the window and separates the LEDs and optically isolates (16). A second baffle (18') is positioned between each of the further LEDs (14).

The same embodiment is illustrated in FIG. 5, which is a transverse cross-section looking from the left hand side in FIG. 4. FIG. 5 shows the outline of the optical baffle (18), which defines the window through which light from the LED (2) illuminates the detection zone of the test strip (10), light is reflected from the detection zone and some of the reflected light is incident on, and detected by, photodiode (6). It is noted that, in practice, some of the light incident upon the detection zone (4) may penetrate into the strip to varying extents. The uppermost surface of the test strip (10) comprises a backing layer (19) of reflective Mylar®, and some of the light incident upon the detection zone (4) may even penetrate as far as, and be reflected by, the Mylar® layer and subsequently be detected by the photodiode (6).

The embodiment described and illustrated in FIGS. 4 & 5 shows an assay result reading apparatus which operates in a reflectance mode. A similar reading apparatus could operate in a transmissive mode, except that in such an embodiment the LED (2) and the photodiode (6) would lie on opposite sides of the strip [and the strip would be supported on a backing layer of transmissive Mylar®]. The window shape would be generally as shown in FIG. 3 for the transmissive mode reader, if the LED (2) and photodiode (6) remained centralized on the intended axis of the detection zone.

Example 3

As explained above, the window shape indicated in FIG. 3 is suitable for embodiments of the invention in which the light source and optical detector are aligned with the central axis of the detection zone when the detection zone is in its intended position. However, other configurations of light source and detector are possible, and the person skilled in the art can determine appropriate window shapes to offset signal roll-off experienced in those configurations, with the benefit of the present disclosure.

Figure 6:
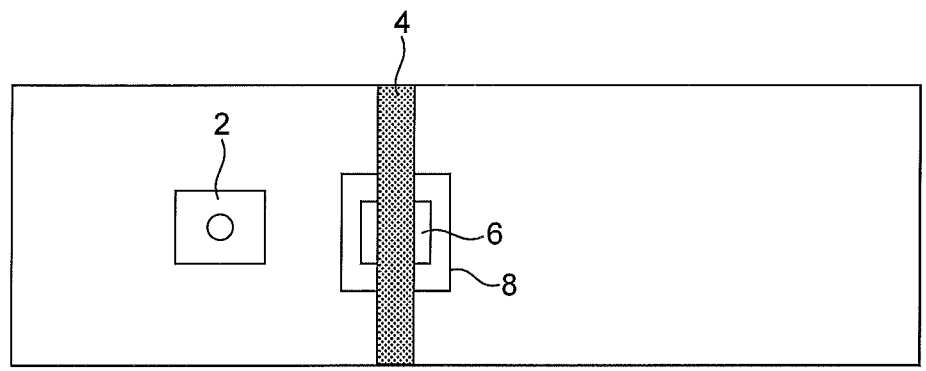
FIG. 6 is a schematic representation of a different embodiment of a prior art assay reading apparatus.

One such alternative configuration is illustrated schematically in FIG. 6. In this alternative configuration the detector (6) is directly aligned with the central axis of the detection zone (4) (when the detection zone is correctly positioned), but the light source (LED 2) is displaced to one side. In this configuration the response of the system will be inherently asymmetric if the detection zone is displaced to either side of its intended position.

In this arrangement the side (20) of the window (8) closer to the LED (2) will receive more light than the side (22) of the window further away. Hence with a square window, if the line detection zone is displaced towards the side (20) of the window (8) closer to the LED (2) the amount of light reaching the photodetector (6), and hence the signal output from the detector, will be attenuated more than when the detection zone is displaced towards the edge of the window further from the LED (2).

Figure 7:
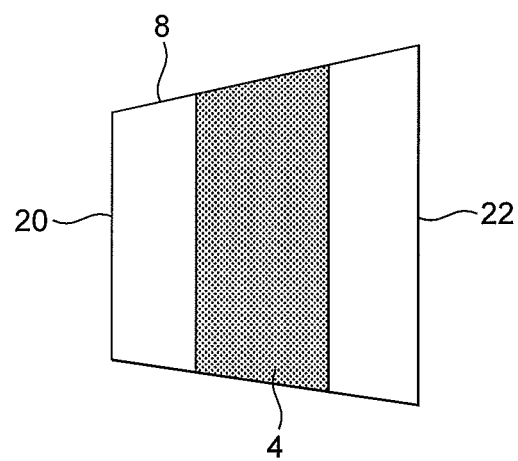
FIG. 7 is a schematic representation of part of an assay result reading apparatus in accordance with the invention, having the configuration of light source, detector, window and detection zone shown in FIG. 6, but with a window shaped so as to reduce the sensitivity of the reading apparatus to minor mis-positioning of the assay device detection zone relative to the window.

In order to correct this problem one would design the window shape to collect less light at the edge nearer to the LED as illustrated in FIG. 7.

The window shape depicted in FIG. 7 shows generally that it would be desirable to have a smaller window height closer to the LED to restrict the light. The actual ratio of height of the window at this edge compared to the other edge, and whether there is a straight line between the two edges (left to right), will depend upon the particular size and positioning of the optical components i.e. the light source, the light detector and the detection zone.

Note that the same optical approach would be taken in this case if the positions of LED (2) and detector (6) were substituted. The short edge would effectively be related to the shortest optical path.

Example 4

The person skilled in the art can establish a suitable window shape for any particular configuration of light source, detection zone and light detector. This example provides one method for determining an appropriate window shape.

Characterize a rectangular window in terms of its spatial sensitivity as follows:

1) Construct a special test strip from minimally reflective (black) material and superimpose on it (in the same orientation as the standard line) a thin line of reflective material. In general, the thinner the better unless it starts to run into noise problems or errors caused by a limit of sensitivity of the detection electronics.
2) Replace the standard strip in the device with this special test strip with (initially) the position of the long edge of the reflective area to be against one edge of the window, but fully contained by the window.
3) Illuminate the LED to a standard light output and record the current from the photodiode.
4) Move the line in increments preferably equal to (or even more preferably less than) the width of the reflective line.
5) Measure the photodiode current again with the LED at the same brightness.
6) Repeat steps 4 and 5 until the reflective portion of the strip is situated (but still contained within) the opposite edge of the window.
7) From the table of results generated then, as appropriate, either
   a. Reduce the height of the window in each lateral position by a factor equivalent to the minimum signal detected level divided by the signal level at the current position; or
   b. increase the height of the window in each lateral position by a factor equivalent to the signal detected at the maximum signal detected divided by the signal level detected in the current position.
8) Clearly, to obtain a smoother edge to the eventual window produced it is possible to interpolate between measurements of the signal sensitivity using well known curve fitting mathematical techniques.

In terms of what measurements to use—a typical window may be about 2 mm wide. "Roll offs" in sensitivity of the order of 10% may be normal. The quality of correction achieved will be related to the thickness of reflective area used and the increment resolution with which it is moved across the window: typically something around 0.2 mm wide moved in increments of 0.1 mm to gain some positional overlap may be appropriate.

As an alternative (and this may be an easier to use method) to the above experimental technique: computer software for optical modeling (such as Zemax) could be used to model the light source, detector and geometry of the system and determine similar information as discovered by using the experimental technique above (calling on modeling techniques such as Monte Carlo analysis) and hence develop by mathematical means similar correction factors.

Example 5

Material

A commercially available Persona® monitor was used to illustrate the invention. The Persona® monitor utilises optical transmission of light through an assay strip to determine the amount of latex bound in a detection zone on the strip. The standard device has a 1 mm wide detection zone appearing within a 2 mm wide window in the optical arrangement of the monitor. To perform the transmission measurement the monitor has an LED light source on one side of the test strip and a photo detector on the other, with both components nominally aligned to the centre of the window which is also the intended centre of the detection zone. Two such test detection windows are utilized within the monitor, one for luteinising hormone (LH) and one for estrone-3-glucuronide (E3G), each window intended to be aligned with a respective detection zone.

Monitor performance was assessed using a standard set of test devices in which lines were printed on assay strips to represent particular intensities of marker captured in the detection zone. The experiment utilized three test devices:

Device 1 (D1)—in which a solid line of 1.1 mm width was printed on the assay strip in each of the two test detection zones. The 1.1 mm line represents the full scale signal in the detection zone. The lines were positioned such that the line centre was coincident with the intended centre of the assay line.

Device D2—as stick D1 except that the line centre was displaced 0.4 mm in one direction from the intended centre of the assay line.

Device D3—as stick D1 except that the line centre was displaced 0.4 mm in the other direction (compared to stick D2) from the intended centre of the assay line.

Baseline Performance

The standard test sticks were utilised to characterise the performance of the monitor when the lines were displaced away from their nominal intended position. The following results were obtained:

| Test Parameter | Relative Signal Intensity (arbitary units) | Notes |
|---|---|---|
| S1(D1) | 54.3 | High signal (1.1 mm line central position) |
| S2(D1) | 55.8 | |
| S1(D2) | 50.9 | 1.1 mm line 0.4 mm offset |
| S2(D2) | 52.2 | |
| S1(D2)/(D1) ratio | 0.94 | Band placement (0.4 mm offset) |
| S2(D2)/(D1) ratio | 0.94 | |
| S1(D3) | 52.6 | 1.1 mm line −0.4 mm offset |
| S2(D3) | 53.5 | |
| S1(D3)/(D1) ratio | 0.97 | Band placement (−0.4 mm offset) |
| S2(D3)/(D1) ratio | 0.96 | |

Examination of the table shows the decrease in signal intensity as the lines were shifted away from their nominal centre position. The average decrease was around 5% of signal.

S1 refers to the performance observed on the LH channel of the monitor while S2 refers to the performance observed on the E3G channel.

The ratios of D2/D1 and D3/D1 are a measure of the sensitivity of the signal intensity to displacement of the detection zone(s) relative to the intended axis. A value of 1.00 for the ratios indicates that the monitor is insensitive to relative displacement of the detection zones.

Note that the difference seen between the displacement in one direction compared with the displacement in the other direction can be explained by minor errors in the exact positioning of the lines during printing/mounting in the test carrier.

Modification of Standard Monitor

The observed performance was utilized to determine the window shape (in accordance with preceding example 4 part 7(a) of the present specification). An improved window shape, (essentially as illustrated in FIG. 3) was determined—the upper and lower edges of the window were shaped to give a smoother transition as only single points either side of the nominal position were available.

A piece of thin, opaque black plastic sheet had the desired, modified window shape cut out. The window scale was set such that the outer (longer) edges of the window corresponded to the standard window height. The plastic mask was then inserted in front of the standard window of the monitor.

Modified Performance

| Test Parameter | Relative Signal Intensity (arbitary units) | Notes |
|---|---|---|
| S1(D1) | 50.7 | High signal (1.1 mm line central position) |
| S2(D1) | 52.0 | |
| S1(D2) | 49.5 | 1.1 mm line 0.4 mm offset |
| S2(D2) | 50.6 | |
| S1(D2)/(D1) | 0.98 | Band placement (0.4 mm offset) |
| S2(D2)/(D1) | 0.97 | |
| S1(D3) | 50.1 | 1.1 mm line −0.4 mm offset |
| S2(D3) | 51.4 | |
| S1(D3)/(D1) | 0.99 | Band placement (−0.4 mm offset) |
| S2(D3)/(D1) | 0.99 | |

Comparison of the table above with the original data shows a significant reduction in the effect of displacing the line centre in both directions. The average decrease in signal intensity was around 2% rather than the originally observed 5%. The ratios of D2/D1 and D3/D1 were much closer to 1.00.

CONCLUSION

Shaping of the window improved the tolerance of the monitor to mispositioning of the lines read in the test windows as predicted.

Only a single point measurement was utilized to determine the drop off in signal as the line was moved away from the nominal position in either direction. As a result a relatively crude modified window shape was developed. Further refinement of the window shape, made possible by additional displacement position measurements, would be expected to give further gains in performance.

The invention claimed is:

1. An assay result reading apparatus comprising a housing that accommodates a lateral flow assay test strip in which a detectable substance tends to accumulate within a detection zone of the lateral flow assay test strip aligned with the housing, the housing having a window therein; a light source which emits light through the window so as to illuminate the detection zone of the lateral flow assay test strip; and a light detector to detect the amount of light reflected and/or transmitted by the detection zone, which amount is at least partly dependent on the amount of detectable substance accumulated in the detection zone; wherein the shape of the window normalizes variations in light intensity and renders the reading apparatus less sensitive to minor mis-positioning of the detection zone due to a test strip insertion, relative to one or more of the window, the light source and the light detector, wherein the window comprises one opposite pair of straight-edged parallel surfaces, and one opposite pair of concave surfaces.

2. The assay result reading apparatus according to claim 1, wherein the assay result reading apparatus comprises the lateral flow assay test strip in a fixed position abutting a surface of the housing and aligned with the housing as an integral part of the assay result reading apparatus.

3. The assay result reading apparatus according to claim 1, wherein the detectable substance comprises a labelled reagent.

4. The assay result reading apparatus according to claim 1, wherein the light source emits light in the visible spectrum and the light detector detects light in the visible spectrum.

5. The assay result reading apparatus according to claim 1, wherein the light source comprises an LED.

6. The assay result reading apparatus according to claim 1, wherein the detector comprises a photodiode.

7. The assay result reading apparatus of claim 1, wherein the shape of the window renders the reading apparatus insensitive to minor mis-positioning of the detection zone, relative to one or more of the window, the light source and the light detector.

* * * * *